(12) United States Patent
Siegle et al.

(10) Patent No.: US 11,660,442 B2
(45) Date of Patent: May 30, 2023

(54) REGULATORY DEVICE AND ASSOCIATED METHOD

(71) Applicants: UNIVERSITY OF PITTSBURGH-OF THE COMMONWEALTH SYSTEM OF HIGHER EDUCATION, Pittsburgh, PA (US); UPMC, Pittsburgh, PA (US)

(72) Inventors: Greg J. Siegle, Wexford, PA (US); David Mayer Lowell Rabin, Pittsburgh, PA (US)

(73) Assignees: University of Pittsburgh-Of the Commonwealth System of Higher Education, Pittsburgh, PA (US); UPMC, Pittsburgh, PA (US)

( * ) Notice: Subject to any disclaimer, the term of this patent is extended or adjusted under 35 U.S.C. 154(b) by 1265 days.

(21) Appl. No.: 16/088,608

(22) PCT Filed: Apr. 3, 2017

(86) PCT No.: PCT/US2017/025702
§ 371 (c)(1),
(2) Date: Sep. 26, 2018

(87) PCT Pub. No.: WO2017/173436
PCT Pub. Date: Oct. 5, 2017

(65) Prior Publication Data
US 2019/0076643 A1    Mar. 14, 2019

Related U.S. Application Data

(60) Provisional application No. 62/316,695, filed on Apr. 1, 2016.

(51) Int. Cl.
*A61N 1/04*        (2006.01)
*A61B 5/00*        (2006.01)
(Continued)

(52) U.S. Cl.
CPC .......... *A61N 1/0452* (2013.01); *A61B 5/0051* (2013.01); *A61B 5/02405* (2013.01);
(Continued)

(58) Field of Classification Search
CPC .............. A61B 5/0051; A61B 5/02405; A61B 5/02416; A61B 5/0533; A61B 5/165; A61N 1/0452
See application file for complete search history.

(56) References Cited

U.S. PATENT DOCUMENTS 9,202,352 B2    12/2015    Levesque
10,228,764 B2    3/2019    Levesque
(Continued)

*Primary Examiner* — Amanda K Hulbert
*Assistant Examiner* — Philip C Edwards
(74) *Attorney, Agent, or Firm* — Philip E. Levy; Eckert Seamans Cherin & Mellott, LLC

(57) ABSTRACT

A peripheral device for regulating neural correlates of arousal and emotion regulation to be worn or held against the body is disclosed. The device can be triggered by either physiological signs or manual intervention and produces cutaneous signals such as vibration or electricity using novel combinations of physiologically reactive frequencies without effort on the part of the user. One embodiment includes combining sensors that measure changes in physiological signals of stress such as speech rate and pitch, galvanic skin response, or heart rate variability, and, using a machine learning algorithm on personalized data, can determine whether these changes are likely to benefit from regulation. If they are outside an idiosyncratic predetermined range, the device produces stimulation and the person will feel regulated if they are touching/wearing the device, or can choose to use the device if it is not currently being touched or worn.

18 Claims, 6 Drawing Sheets

(51) Int. Cl.
 *A61B 5/024* (2006.01)
 *A61B 5/0533* (2021.01)
 *A61B 5/16* (2006.01)
 *A61N 1/36* (2006.01)
 *A61N 1/00* (2006.01)
 *A61B 5/01* (2006.01)

(52) U.S. Cl.
 CPC ........ *A61B 5/02416* (2013.01); *A61B 5/0533* (2013.01); *A61B 5/165* (2013.01); *A61B 5/441* (2013.01); *A61N 1/00* (2013.01); *A61N 1/0456* (2013.01); *A61N 1/36031* (2017.08); *A61B 5/01* (2013.01)

(56) References Cited

U.S. PATENT DOCUMENTS

| | | |
|---|---|---|
| 10,248,850 B2 | 4/2019 | Rihn et al. |
| 10,289,201 B2 | 5/2019 | Cruz-Hernandez |
| 11,260,198 B2 | 3/2022 | Rabin et al. |
| 2003/0001008 A1 | 1/2003 | Kitov |
| 2003/0083599 A1* | 5/2003 | Kitov ................. A61H 23/0236 601/84 |
| 2007/0219470 A1* | 9/2007 | Talish .................... A61H 23/00 601/2 |
| 2012/0149973 A1* | 6/2012 | Holloway ............ A61K 31/197 600/28 |
| 2014/0148872 A1* | 5/2014 | Goldwasser ....... A61N 1/36034 607/45 |
| 2014/0163439 A1* | 6/2014 | Uryash ............ A61B 17/22004 601/47 |
| 2014/0232534 A1 | 8/2014 | Birnbaum et al. |
| 2015/0335288 A1 | 11/2015 | Toth et al. |
| 2016/0074278 A1 | 3/2016 | Muench et al. |
| 2017/0224990 A1 | 8/2017 | Goldwasser et al. |
| 2017/0296429 A1 | 10/2017 | Mayo et al. |
| 2018/0233226 A1 | 8/2018 | Ramsay et al. |
| 2019/0171292 A1 | 6/2019 | Levesque |
| 2020/0147339 A1 | 5/2020 | Mayo et al. |

* cited by examiner under 35 U.S.C. § 119(e)
REGULATORY DEVICE AND ASSOCIATED METHOD

CROSS-REFERENCE TO RELATED APPLICATION

This application claims priority under 35 U.S.C. § 119(e) from U.S. provisional patent application Ser. No. 62/316, 695, entitled "Emotion Prosthetics" and filed on Apr. 1, 2016, the contents of which are incorporated herein by reference.

GOVERNMENT CONTRACT

This invention was made with government support under grant #s MH082998 and MH096334 awarded by the National Institute of Health and under grant #IIP-1449702 awarded by the National Science Foundation. The government has certain rights in the invention.

BACKGROUND OF THE INVENTION

1. Field of the Invention

This application generally relates to devices that can be held against the body or attached to something connected to the body to promote change in at least one of emotional state, arousal state, and cognition.

2. Background of the Invention

Stress is a specific global impairing problem with no globally effective solution. Approximately a third of the US population describes having more stress than they would like to without effective coping strategies. Chronic unmanaged stress results in time missed from work and impaired productivity, and can lead to debilitating mental and physical illnesses from depression and anxiety to heart disease and dementia. Interventions for stress primarily consist of psychological therapies/techniques and drug/prophylactic therapies. Psychological techniques (e.g., as taught in psychotherapy or meditation) depend on the user attending to their mental events and emotions, and applying learned techniques in the moment. Literature suggests such interventions do not work for many people. For example, individuals who tend to ruminate do most poorly in even the best psychological therapies. Drug/prophylactic therapies depend on an agent taken at one time point to have effects much later when they are needed. These treatments have many side effects and are often addictive. A common observation is that most psychiatric medications, in tolerable doses, are not strong enough to prevent or even improve in-the-moment reactivity to stressors. What is needed is an intervention that becomes effective at times of stress, intervenes without requiring strong presence of mind on the part of the user, and then stops being active when the stress dissipates. It would be desirable to provide a technology that is applicable to solving problems throughout multiple fields and markets broadly spanning from the medical field (e.g., psychiatry, psychology), to enterprise applications (e.g., HR and training), military applications, consumer models (e.g., stress management), and the entertainment business (e.g., emotionally augmented adaptive virtual reality).

SUMMARY OF THE INVENTION

The invention regards regulation of physiological states using cutaneous transducers (vibration or electricity) at times of stress or deviation from a target emotion state (e.g., "calm"). Thus, included in the invention are 1) regulatory devices that provide specific types of physiologically reactive stimulation useful for regulating arousal and stress, 2) invocation via manual switching or sensors and algorithms to determine its need, and 3) individualized calibrations and learning algorithms to determine optimal parameters for sensing and regulating a given person's arousal, stress, or distance from a target physiological state such as calm. A more general utility of the same technologies regards techniques that associate physiological reactivity profiles with stored idiosyncratic emotion states (e.g., "calm"), yield dynamic quantification of distance from these target states, and provide physiological stimulation that returns users to these target emotion states via closed loop stimulation.

According to an aspect of the present intervention, a regulatory device touching the skin of a user, or something that is touching the skin or body of the user, provides stimulation at frequencies demonstrated in the published literature to change sympathetic and parasympathetic tone. The device can be worn, e.g., on a wrist, the neck, or the sternum, all of which have been demonstrated to yield increases in vagal/parasympathetic tone or sympathetic tone with certain frequencies of cutaneous oscillation. The transducer for cutaneous oscillation is strong enough to produce non-ignorable signals. Electricity and vibration can both serve that function. The invention thus includes software for generating an acoustic signal with specific oscillatory characteristics, a transceiver (e.g., Bluetooth receiver) for acoustic signals generated, by the device wirelessly, an amplifier, and any tactile transducer capable of feeding the amplified acoustic signal to the body in a way that is not ignorable.

The mechanisms by which vibration and electrical stimulation can induce changes in stress and parasympathetic tone are well described in the literature. The skin has other receptors that process touch (mechanoreceptors), pain (nociceptors), pleasure (c-tactile fibers) and temperature (thermoreceptors). Information gathered by skin receptors travels to the brain's somatosensory cortex and in parallel, to areas of the brain involved in cognitive processes, motor processes, social processes, and networks more involved in emotional functions, including recognizing and generating emotion (the amygdala, insula, and striatum, for example), and regulating emotion (the prefrontal cortex, for instance). (Davidson, 2000, American Psychologist, 55(1196-1214). Emotions can be generated not just from present inputs but from our interpretation of bodily cues (Damasio, 1999, xii, 386 p.) based on previous experiences as well. There are numerous other pathways by which tactile stimulation could affect brain function. For example, deep tactile stimuli can affect specific nerves directly yielding predictable neural effects. Slow moving touch around the carotid sinus (e.g., via "carotid massage") can potentiate vagus nerve function (Ha, et al., 2015, Am J Emerg Med, 33(7), 963-5, McDonald, et al., 2014, J Am Geriatr Soc, 62(10), 1988-9, Laine Green and Weaver, 2014, J Clin Neurosci, 21(1), 179-80, Cronin and Blake, 2011, J Cardiovasc Electrophysiol, 22(5), 600) possibly via direct nerve stimulation or other routes such as stimulation of underlying muscles (Scali, et al., 2013, Spine J, 13(5), 558-63). Manual therapies like massage have implicated varying mechanisms such as release of endocannabinoids (Lindgren, et al., 2015, BMC Res Notes, 8(504). Different styles of massage to the same area have been found to activate different brain networks (Sliz, et al., 2012, Brain Imaging Behav, 6(1), 77-87) suggesting a more complex picture of the touch-brain relationship. Deep chest pressure (e.g., as used in "hug machines") directly appears to affect baroreceptors (Edelson, et al., 1999, Am J Occup Ther, 53(2), 145-52) yielding decreased blood pressure and feelings of calm. Accupressure, which involves deep touch has been conceptualized from a variety of perspectives and also appears to affect peripheral physiology such as heart rate variability (McFadden, et al., 2012, Complement Ther Med, 20(4), 175-82. Huang, et al., 2005, Am J Chin Med, 33(1), 157-64) suggesting potential vagus nerve involvement. Electrical stimulation, in particular, activates lamina 1 fibers (McMahon and Wall, 1984, Pain, 19(3), 235-47) which convey pain, itch, sensual touch, and temperature through the spinal cord to the primitive brain areas like the amygdala, yielding emotional reactions and, through the thalamus, to the insula to yield awareness of our body's reactions (Craig, 2002, Nat Rev Neurosci, 3(8), 655-66). The insula passes this info on to cortical regions that govern our attention and emotion regulation such as the orbitofrontal cortex (Cavada, et al., 2000, Cereb Cortex, 10(3), 220-42). Electricity likely produces opioids (Chen, et al., 1996, J Pharmacol Exp Ther, 277(2), 654-60) along with beta endorphins (Bossut, et al., 1986, Am J Vet Res, 47(3), 669-76), which affect emotion and pain thresholds (Lundeberg, at al., 1989, Am J Chin Med, 17(3-4), 99-110). Electrical stimulation also activates the locus coeruleus (Snow, et al., 1999, Arch Ital Biol, 137(1), 1-28) which is responsible for norepinephrine production which could moderate stress responses.

In particular, this invention relies on beat frequencies in the 0.01-20 Hz range which are well-documented to be psychophysiologically reactive. Slow whole-body vibration, in the 0.01 to 0.3 Hz range, is associated with increased ratings of pleasantness and increased parasympathetic tone at lower frequencies with increasing predominance of sympathetic tone approaching 0.6 Hz (Uchikune, 2004, Journal of Low Frequency Noise Vibration and Active Control, 23(2), 133-138. Uchikune, 2002, Journal of Low Frequency Noise Vibration and Active Control, 21(1), 29-36). That said, whole-body stimulation at 1 Hz has been observed to produce increased parasympathetic tone (Takahashi, et al., 2011, J Hum Ergol (Tokyo), 40(1-2), 119-28), with the specific observation of being able to produce vibration-synchronized heart beats. The 0.1 Hz frequency may be particularly useful stimulate at to promote parasympathetic tone, based on biofeedback literature. The highest amplitude of RSA is achieved at 0.1 Hz (6 breaths/minute), because this is the optimal respiratory rate for oxygenation and removal of $CO_2$ from the body. As such, 0.1 Hz is known as the frequency of cardiac resonance (high-amplitude synchronous oscillations at a single frequency). This cardiac resonance is achieved with generally lower frequency stimulation in tall people/men and generally higher frequency stimulation in smaller people/women (Vaschillo, et al., 2006, Appl Psychophysiol Biofeedback, 31(2), 129-42). Thus, it has been suggested that "any source of rhythmic stimulation that affects the cardiovascular system should produce the same effect (achieving cardiac resonance of 0.1 Hz)." (Lehrer and Gevirtz, 2014, Front Psychol, 5(756). Thus, stimulation via rhythmic muscle tension at 0.1 Hz has been found to increase high frequency heart rate variability (Lehrer, et al., 2009, Biol Psychol, 81(1), 24-30, Vaschillo, et al., 2011, Psychophysiology, 48(7), 927-36) as has rhythmic visual stimulation at 0.1 Hz (Vaschillo, et al., 2008, Psychophysiology, 45(5), 847-58). Wrist-worn vibratory cues in this range have been shown to affect hemodynamics following stressful tasks (Nogawa, et al., 2007, Conf Proc IEEE Eng Med Biol Soc, 2007(5323-5). Increased heart rates have been found for whole-body vibration at lower frequencies (3-6 Hz) (Maikala, et al., 2006, Int Arch Occup Environ Health, 79(2), 103-14) though individual differences in cardiac effects act these frequencies have been observed (Ullsperger and Seidel, 1980, Eur J Appl Physiol Occup Physiol, 43(3), 183-92). Vibration in the 6-10 Hz range appears to decrease parasympathetic tone, as measured by high frequency heart rate variability (Jiao, et al., 2004, Int Arch Occup Environ Health, 77(3), 205-12, Bjor, et al., 2007, Int Arch Occup Environ Health, 81(2), 193-9) and is specifically associated in increased low-to-high frequency heart rate variability rations, potentially suggestive of increased sympathetic tone (Watanabe and Ujike, 2012, Health, 4(11), 1029-1035). Increasingly peripheral stimulation at 10 hz is being used to modulate activity in the vagus nerve, which governs heart-rate variability, and thus parasympathetic tone (Ma, et al., 2016, J Neurol Sci, 369(27-35, Bauer, et al., 2016, Brain Stimul, 9(3), 356-63. Jiang, et al., 2016, Neurochem Int. 97(73-82, He, et al., 2016. Cardiovasc Ther, 34(3), 167-71).

This invention also relies on base frequencies in the 20-300 Hz range which are also well-documented to be physiologically reactive. A large literature devoted to whole-body vibration has primarily examined the 20-36 Hz range, which is generally associated with increased heart rates (e.g., Gojanovic, et al., 2014, Physiol Res, 63(6), 779-92, Cochrane, et al., 2008, Arch Phys Med Rehabil, 89(5), 815-21). 25 Hz whole-body vibration is associated with decreased heart rate and baroreceptor activity consistent with parasympathetic response, particularly in obese people (Dipla, et al., 2016, Exp Physiol, 101(6), 717-30), though another study found no change in HRV for 20-36 Hz following exercise (Cheng, et al., 2010, J Sports Med Phys Fitness, 50(4), 407-15). That said, electrical stimulation in the 10 Hz range has been found to produce increased HF HRV (Stein, et al., 2011, Auton Neurosci, 165(2), 205-8). Typical personal massage devices operate at about 100 Hz (Prause, et al., 2012, Sexual and Relationship Therapy, 0.27(1), pp), with the goal of producing subjective and muscle relaxation. Stimulation at this frequency activates the posterior insula (Coghill, et al., 1994, J Neurosci, 14(7), 4095-108) which is associated with increased attention to interoception, as promoted in many meditative traditions. Vibrator massage is associated with both increased heart rate but also increased theta and alpha EEG associated with relaxation (Diego, et al., 2004, Int J Neurosci, 114(1), 31-44). Electroacupuncture produces the sensation of rapid vibration; stimulation at 100 Hz is associated with increased subsequent high frequency heart rate variability (Hideaki, et al., 2015, Acupunct Med, 33(6), 451-6) though TENS unit stimulation at 100 Hz has been observed to produce decreased high frequency heart rate variability (Stein, et al., 2011, Auton Neurosci, 165(2), 205-8). Facial vibration at 89 Hz has specifically been associated with increased parasympathetic tone (Hiraba, et al., 2014, Biomed Res Int, 2014 (910812).

According to another aspect of the present intervention, the regulatory device combines low and high frequencies described as physiologically reactive in the literature to yield unique superadditive sensations. For example, complex musical and complex vibroacoustic stimuli have been shown to modulate a variety of neural responses associated with vagal tone (Bergstrom-Isacsson, et al., 2014, Res Dev Disabil. 35(6), 1281-91). Vibroacoustic stimulation has been shown to affect electroencephalographic recordings as well as positive mood (Sandler, et al., 2016, Brain Topogr, 29(4), 524-38).

According to another aspect of the present intervention, use of intervention is invoked by detecting a predetermined condition, such as a manual switching on the regulatory device or the detection by the regulatory device of a predetermined condition in the form of physiological changes associated with an increase or decrease in arousal or stress. Manual switching is done by invoking software, e.g., on a smartphone, or via a switch on the device. Many physiological parameters can be used to detect emotion and arousal states such as stress or fatigue, including but not limited to changes in vocal tone, galvanic skin response, and heart rate variability, pupil dilation, and gamma band EEG. These parameters are interpretable in the presence of a baseline measurement, e.g., of stressed, relaxed, and fatigued states to which similarities on assessed parameters can be inferred. The invention thus includes software for establishing an individual's resting, stressed, fatigued, or user-defined target profiles on available physiological measurements, and for comparing, in real time, measurements of derived parameters to these states, and inferring the extent to which a current state appears similar to those stored states (e.g., stress or fatigue) with respect to individually titrated parameters.

According to another aspect of the invention, individuals differ in the extent to which different frequencies affect physiological reactions. Thus the invention includes calibration procedures to assess subjective and, when possible, physiological reactivity to different combinations of frequencies to allow best-suited regulatory stimulation.

According to another aspect of the invention, an individual's physiological features associated with potentially user-defined emotion and arousal states along with stimulation parameters that optimally restore those states can be stored in a library for later recall by that or another individual. For example, if an individual is having a particularly good day, physiology associated with that state can be stored, and stimulation parameters that optimally maintain that state or move from stressed or fatigued states towards that state can be stored in the library for later recall.

DESCRIPTION OF THE PREFERRED EMBODIMENTS

In the figures to be discussed, the associated boxes and arrows represent functions of the process according to the present invention, which may be implemented as electrical circuits and associated wires or via wireless protocols such as Bluetooth, which transport acoustic signals. Alternatively, one or more associated arrows may represent communication (e.g., data flow) between software routines, particularly when the present method or apparatus of the present invention is a digital process.

Regulatory Device

Figure 1:
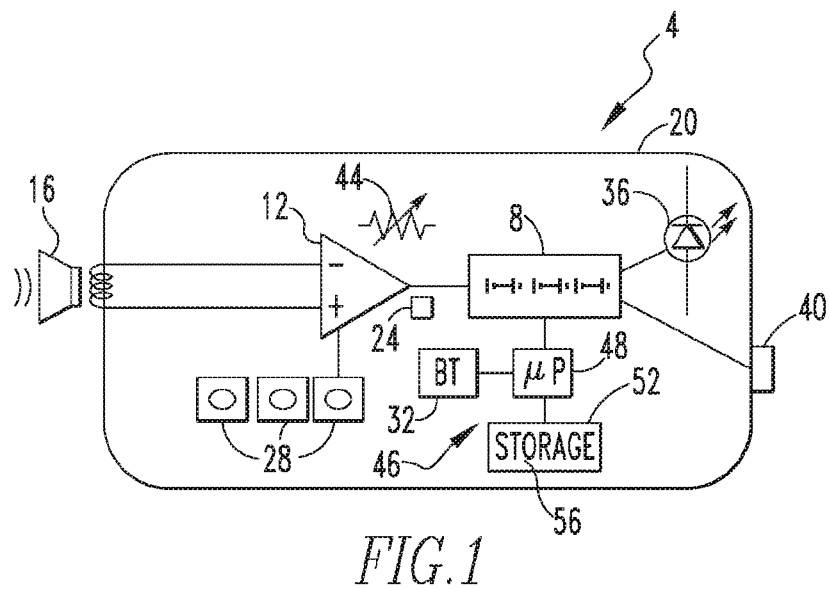
FIG. 1: Example implemented regulatory device with Vibratory Transducer.

The regulatory device 4 depicted generally in FIG. 1 includes a rechargeable 6000 mAh Li-Ion Battery Pack 8, 12V DC, With Charger, a DC10-22V AC 10-16V 25 W 4 Ohm Audio Speaker HIFI Digital Amplifier Board 12 w/SD card input, a tactile transducer 16 which, for instance, is a Bass Shaker 8 Ohm which can be extended from the interior via wires from the amplifier board 12, a 3D printed casing 20 with beveled opening for wires from the transducer 16, an SD Card 24 containing pre-loaded stimulation waveforms including: 20, 33, 40, 89, 100, 200 Hz modulated by 0, 0.1, 1, and 4 Hz, Buttons 28 for manually scrolling through pre-loaded waveforms and for providing other inputs to the regulatory device 4, a Bluetooth receiver 32, an LED 36 showing whether the regulatory device 4 in an ON state, a Switch 40 to turn the regulatory device 4 to the ON state, a Dial 44 to manually modulate waveform intensity, and a processor apparatus 46 having a processor 48 and a storage 52 having stored therein software in the form of a number of routines 56 that generate a number of oscillation signals. As employed herein, the expression "a number of" and variations thereof shall refer to any non-zero quantity, including a quantity of one. The Bluetooth receiver 32 is most advantageous when the device that generates the oscillation signals is remote from the casing 20, such as a smart phone or other computerized device, which communicates via its own Bluetooth transmitter the oscillation signals to the Bluetooth receive 32. The routines 56 can be in the form of a non-transitory storage medium which, when executed on computerized device, causes the computerized device to perform operations such as the operations noted herein.

The regulatory software routines 56 emit a combination of sine wave oscillations of different frequencies to result in a beat frequency that is output to the user. The combination of oscillations comprise a main oscillation in the range of about 20-300 Hz and at least one modulation oscillation in the range of about 0.01-10 Hz yielding a beat output that provides to the user a feeling of slow waves of stimulation at a frequency determined to be arousing or calming via the calibration software. Any of multiple base waveform types described as being physiologically active in the literature (the implemented device in FIG. 1 can generate as a main oscillation any of 20, 33, 40, 89, 100, and 200 Hz) and modulatory frequencies also referenced in the literature (the implemented device in FIG. 1 can also generate modulation oscillations of 0.1, 1, and 4 Hz), any of which can be selected via the buttons 28 on the device in FIG. 1 or an external software program that may be executed on, for instance, a smart phone or any other remote computerized device.

The Bluetooth receiver 32 pairs with whatever device generates the chosen waveforms via external software that runs on a computer or smartphone.

The battery 8 is rechargeable and is sufficient to power the amplifier 12 and transducer 16, e.g., 6000 mAh Li-Ion battery pack.

The amplifier 12 boosts the oscillation signals to a level that is useable by the transducer 16. For vibratory stimulation, which is applied as an output to the body of the user, the amplifier 12 converts the oscillation signals to a level that a 20 W 8 ohm tactile transducer can faithfully reproduce. For electrical stimulation, which is applied as an output to the user's skin, the amplifier converts audio signals to pulse-width-modulated versions (250 μs pulses separated by 5 μs gaps) to prevent skin heating, using standard algorithms, and amplifies them to a physiologically detectable threshold (approx. 2 mAmps) and includes optical isolation and voltage limitation for safety.

The vibratory tactile transducer 16 is designed to be used over any area of the body, which might respond to oscillations produced by the software. The tactile transducer 16 may also deliver whole-body vibrations by being attached to a chair or bed. By way of description and not limitation, FIG. 1 illustrates one embodiment of one vibratory transducer. The vibratory transducer 16 is to be used on the neck, sternum, wrist or another user-determined position and is described herein as being a device that can be used, for instance, at will by resting a body part (e.g., neck when lying down or wrist when in a chair) on the device or, for instance, by holding it against the body (e.g., sternum). The tactile transducer 16 is capable of generating low frequency oscillations (to 20 Hz) with sufficient displacement to be not-easily-ignored, and is covered by a sleeve that can be removed and cleaned easily and which provides insulation from the bare metal of the transducer (e.g., fleece).

Figure 2:
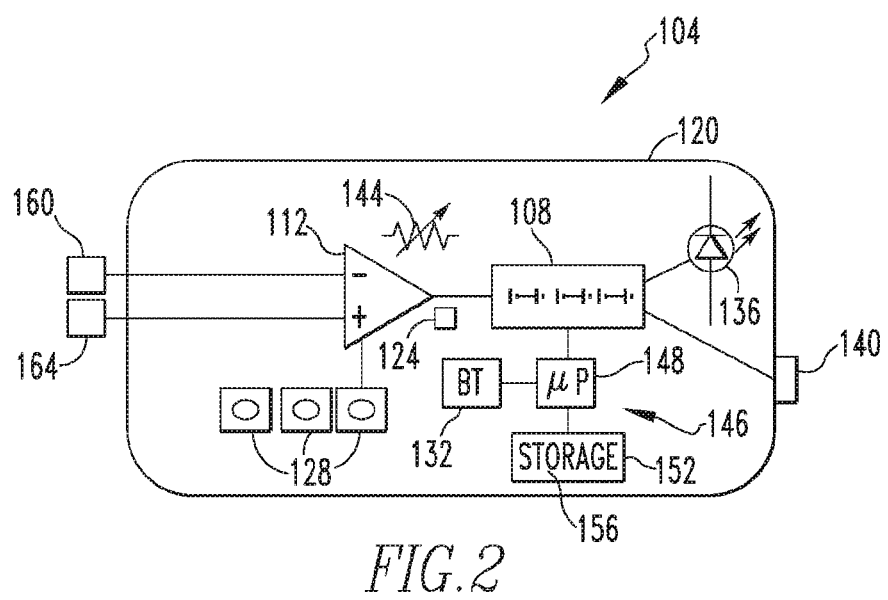
FIG. 2: Example implemented regulatory device with Electrical Transducer
Figure 3A:
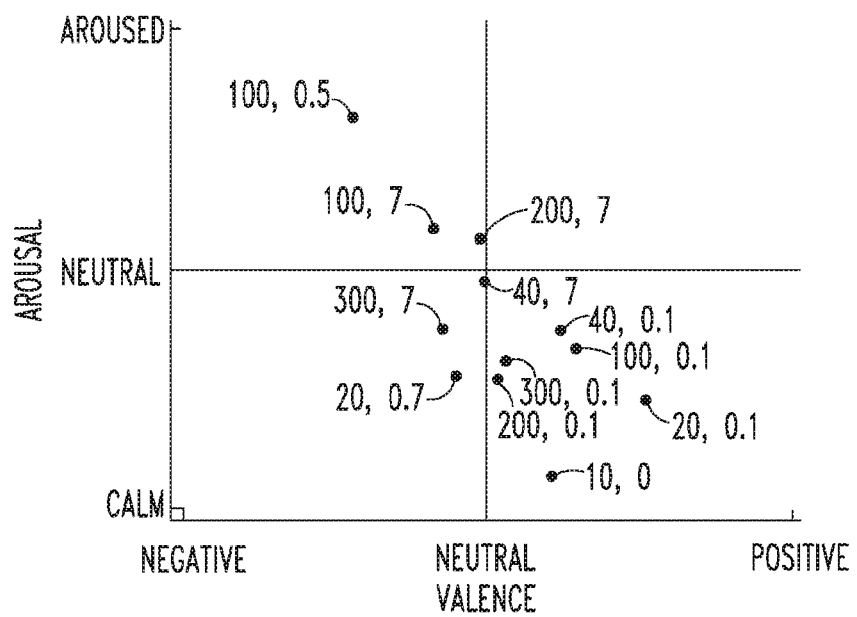
FIGS. 3A and 3B: Data showing average valence and arousal ratings associated with multiple types of stimulation in 38 volunteers experiencing chest and wrist stimulation using combined oscillations, indicated as main frequency, modulating frequency.
Figure 3B:
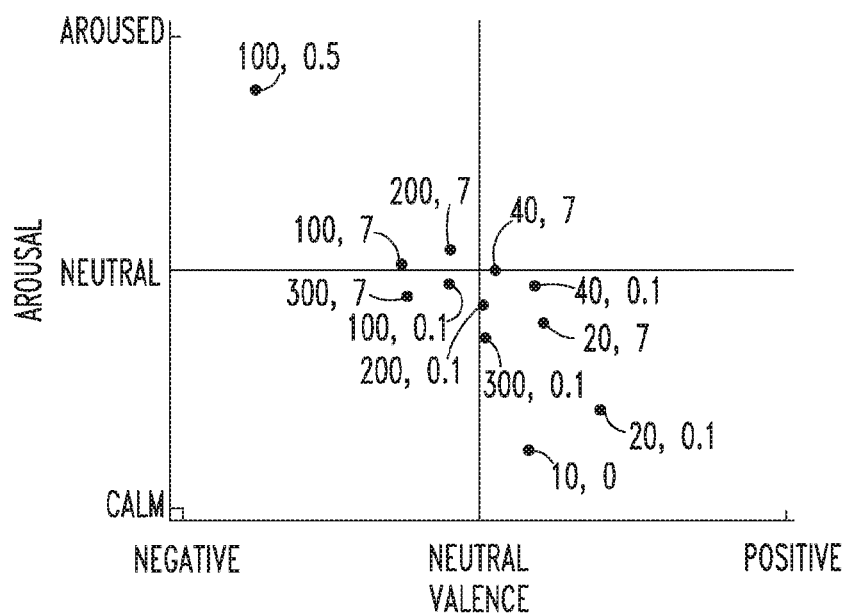

Another regulatory device 104 depicted generally in FIG. 2 is similar to the regulatory device 4, except that the regulatory device 104 includes an electrical transducer. The regulatory device 104 includes a 9V alkaline battery 108, amplifier 112, and an electrical transducer 116 which, for instance, is a pair of adhesive electrodes 160 and 164 which can be extended from the interior via wires from the amplifier board 112, a 3D printed casing 120 with beveled opening for wires from the transducer 116, an SD Card 124 containing pre-loaded stimulation waveforms including: 20, 33, 40, 89, 100, 200 Hz modulated by 0, 0.1, 1, and 4 Hz, Buttons 128 for manually scrolling through pre-loaded waveforms and for providing other inputs to the regulatory device 104, a Bluetooth receiver 132, an LED 136 showing whether the regulatory device 104 in an ON state, a Switch 140 to turn the regulatory device 104 to the ON state, a Dial 144 to manually modulate waveform intensity, and a processor apparatus 146 having a processor 148 and a storage 152 having stored therein software in the form of a number of routines 156 that generate a number of oscillation signals. The electrical transducer regulatory device 104 is illustrated as being a wearable device and is to be worn on the wrist of the user. It consists of two electrodes 160 and 164 that allow the pulse-width modulated signal from the amplifier to pass from one electrode to the other in the form of a voltage between the electrodes 160 and 164 applied to the skin of the user. FIG. 2 illustrates an exemplary embodiment of the electrical transducer regulatory device 104 for communications of oscillations to the skin of the user.

Initial data supports the use of a vibratory device for regulating stress and its physiological correlates. In an experiment with N=38 individuals of whom 9 were associates and 29 were community participants who were compensated for participation, vibratory stimulation at a main frequency of 100 Hz modulated by a modulation frequency of 0.1 Hz, delivered to the wrist, improved performance reliably ($p<0.05$) and, to the chest, marginally ($p<=0.1$) during a stressful (paced auditory serial attention) task above and beyond a no-stimulation condition for those whose performance was at least moderate (above 1-standard deviation below the mean) during the no-stimulation condition. Vibration at this frequency also moderated changes in heart-rate variability (which is a proxy for parasympathetic tone), with statistically significant ($p<0.05$) increases in heart rate variability delivered to the wrist in the full sample and delivered to the sternum in the compensated sample ($p=0.09$ in the full sample). Vibration at this frequency delivered to the sternum also decreased self-reported stress in those whose stress was at least moderate (above 1 standard deviation below the mean) compared to the no stimulation condition ($p<0.05$).

Physiological Detection and Calibration

The physiological detection suite involves using custom and commercial software and hardware to acquire physiological parameters and analyzing them in real time to detect the onset of individualized signatures of stress, fatigue, or other (e.g., user specified) emotion or arousal states.

Figure 4:
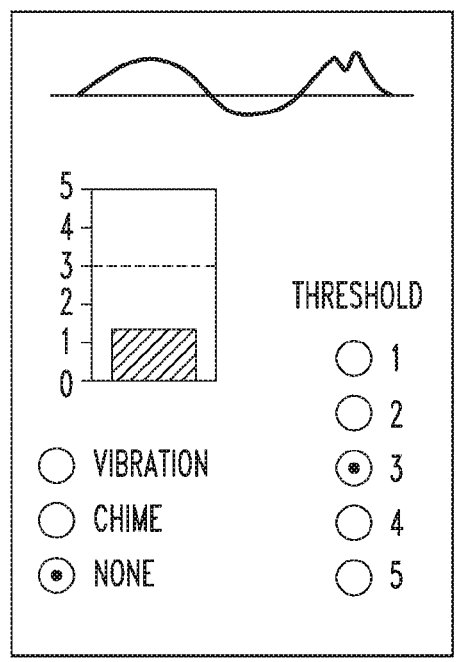
FIG. 4: Example of user interface of software for detection of physiological stress for use with any commercial hardware that records skin conductance and pulse plethysmograph, e.g., Arduino or Bitalino, the data from which can be read. e.g., as a serial stream.

FIG. 4 shows an example of implemented software for detection of physiological profiles associated with an emotion state and generation of reactive stimulation. FIG. 4 depicts a user interface, illustrated based on a screen capture of the software, wherein the user has selected a threshold of three, as is indicated by the "THRESHOLD" indicator, and which is reflected by the dashed line in the bar graph of FIG. 4. An exemplary stress level pattern is depicted at the top of FIG. 4, and the bar indicator in the bar graph demonstrates that the threshold has not been reached. It is noted that FIG. 4 further depicts the user-selectable option to have either a tactile output in the form of a tactile-vibration/electrical stimulation or an audible output in the form of a chime when the user is determined to be in a stressed state. In the event of such a chime or no output, a user can manually enter an input using the buttons to trigger the outputting of the therapeutic stimulation. Alternatively, the user can select "NONE", which is selected in FIG. 4. The event of the detected state of the user in a being stress (or other user selected emotion/arousal) condition with "Vibration" selected, will automatically result in outputting of the associated calibrated therapeutic stimulation.

In one implementation, software for detection of physiological states takes in pulse plethysmograph and galvanic skin response (GSR) inputs, sampled at 1000 Hz, from existing hardware (e.g., Bitalino, Arduino) implemented as generic serial streams. The pulse plethysmograph detects a heartbeat signal that is representative of the heartbeat of the user.

GSR data are preprocessed via spike removal and smoothing (4 second kernel) to yield a smooth running estimate of GSR which is associated with sympathetic nervous system reactivity and stress.

Plethysmograph data are preprocessed via spike removal and peak detection to yield heartbeats which are converted to an inter-beat interval series. The inter-beat series includes a time duration between each successive beat in the detected heartbeat signal.

The inter-beat interval series is subjected to calculation of heart rate (#beats per second).

The inter-beat interval series for 30 seconds is subjected to continuous Morlet waveform transform to yield a running estimate of power in the high frequency heart rate variability (HF-HRV) band (0.18-0.4 Hz), which is associated with parasympathetic nervous system activity and emotion regulation capability, and which can be referred to as an emotional regulation parameter or value. It is noted that other spectral analysis techniques such as Fourier transformation and the like can be employed without departing from the spirit of the disclosed and claimed concept.

One aspect of the algorithm for detection of physiological stress includes quantifying change or slope over a period of time, i.e., 100 ms to 30 seconds, in physiological parameters to detect state onset.

The algorithm for detecting physiological stress is initially seeded for stress detection as reflecting increasing detected current physical parameters such as GSR or heart rate without a corresponding or subsequent change in HF-HRV, i.e.:

$$\text{estimated-stress} = \beta_0 + \beta_1 \Delta GSR_{5\ seconds} + \beta_2 \Delta \text{Heart Rate}_{5\ seconds} - \beta_3 |\Delta HF\text{-}HRV_{5\ seconds}|$$

where the coefficients are initially $\beta_0=0$, $\beta_1=0.5$, $\beta_2=0.5$, $\beta_3=1$ and GSR, HR, and HF-HRV are normalized based on their mean and variability during an initial resting calibration period of 30-seconds. Other detected current physical parameters could include a number of audio parameters that are representative of vocal stress, and other such parameters.

Another aspect of the algorithms includes a calibration operation using software that guides the user to experience resting, stressed, fatigued or other user-specified states, and which includes brief exposure to a stress induction known to provoke increases in sympathetic tone and decreases in parasympathetic tone (e.g., paced serial attention task), to yield an individually calibrated profile for these states (e.g., "stress profile"). For instance, a number of calibration physical parameters of the user such as heart rate signal, GSR signal, and other such parameters, may be detected and stored in the storage 52. The software that performs the guiding can be executed on the regulatory device or can be deployed on a smart phone or other computerized device remote from the regulatory device.

Another aspect of the algorithms includes machine learning to derive individualized best-fit profiles for what stress-onset, fatigue onset, or other user-determined states look like for the individual. In the implemented software, as an example, a machine learning algorithm such as a three-layer pattern recognition neural network with 8 input nodes, 4 hidden nodes, and 1 output node is used to estimate how GSR, Heart Rate, HF-HRV, and estimated change in each of these in the previous 5 seconds combine to predict based on the calibration task described in the preceding paragraph. Effectively this algorithm allows a quantized (sigmoid) ridge-regression estimation of parameters for main effects of each of these parameters, and their potential n-way interactions:

$$\text{estimated-stress} = \beta_0 + \beta_1 \Delta GSR_{5\ seconds} + \beta_2 \Delta \text{Heart Rate}_{5\ seconds} + \beta_3 |\Delta HF\text{-}HRV_{5\ seconds}| + \beta_4 GSR_{5\ seconds} + \beta_5 \text{Heart Rate}_{5\ seconds} + \beta_6 HF\text{-}HRV_{5\ seconds} + \beta_7 \Delta GSR_{5\ seconds} * \Delta \text{Heart Rate}_{5\ seconds} + \beta_8 \Delta GSR_{5\ seconds} * |\Delta HF\text{-}HRV_{5\ seconds}| \ldots + \beta_N \Delta GSR_{5\ seconds} * \Delta \text{Heart Rate}_{5\ seconds} * |\Delta HF\text{-}HRV_{5\ seconds}| GSR_{5\ seconds} * \text{Heart Rate}_{5\ seconds} * HF\text{-}HRV_{5\ seconds}$$

To derive beta weights for the preceding equation, stress values are set to zero during rest and one (1) during the target state, e.g., stress. Thus, "estimated-stress" represents the extent to which a current state is more like the stress vs the resting state. The same type of analysis can be performed for a fatigue or user-specified period. The various β coefficients that are derived through the use of the pattern recognition neural network form a part of the individually calibrated profile that can be used to detect the onset of a period of stress or fatigue. It is understood that additional elements can be added to the above equation in order to derive additional coefficients for use with calibration physical parameters and current physical parameters that are indicative of vocal stress in the user.

Another aspect of the algorithms includes real-time comparison of incoming physiological data in the form of current physical parameters of the user to the individualized best-fit profiles to determine when an individual is beginning to look stressed, fatigued, or a critical distance from a user defined state, so as to trigger the delivery of therapeutic stimulation. Stimulation is signaled whenever the stress index is outside 1.5 standard deviations from its mean, which refers to the aforementioned threshold of "3" in FIG. 4. Stimulation is signaled at lower and higher stress levels if the threshold is set lower or higher, respectively, than "3".

Figure 6:
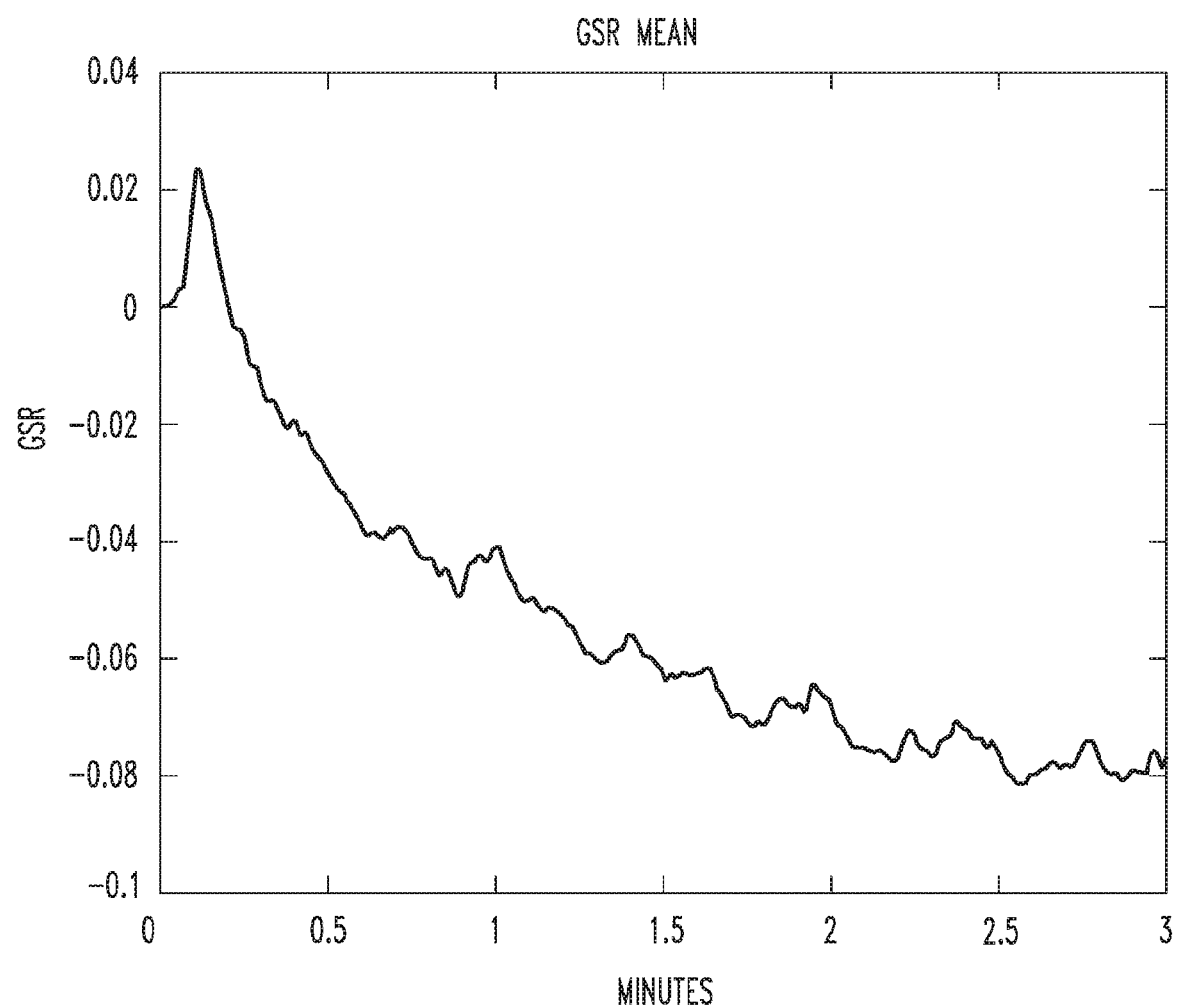
FIG. 6: Data showing clear physiological changes associated with stress onset that can easily be classified by looking at slopes of change.
Figure 7A:
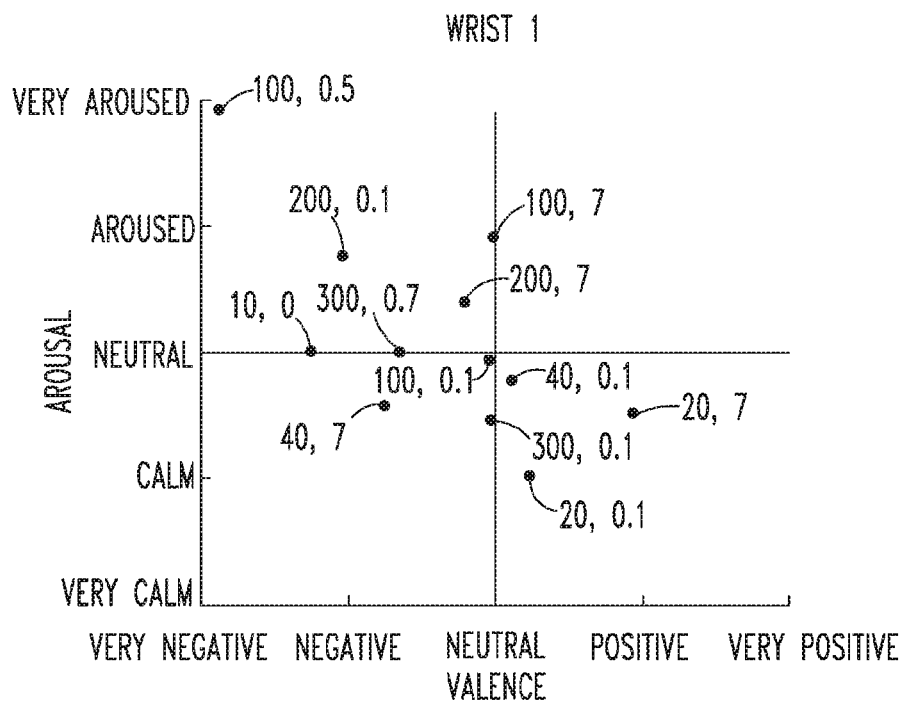
FIGS. 7A, 7B. 7C, and 7D: Data showing individual differences in which patterns are most calming and arousing for different individuals, supporting the utility of individual customization.
Figure 7B:
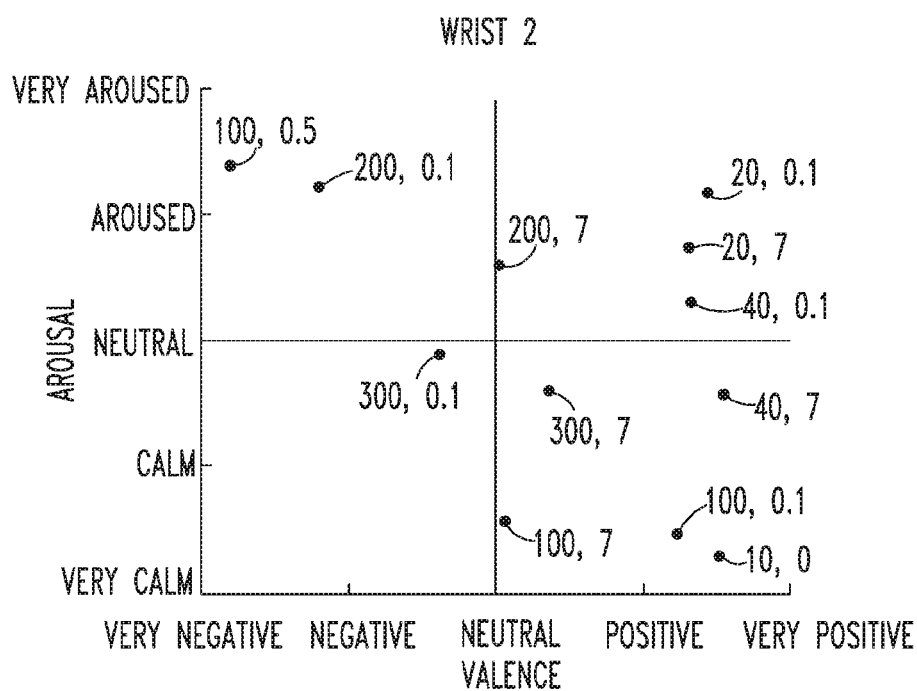
Figure 7C:
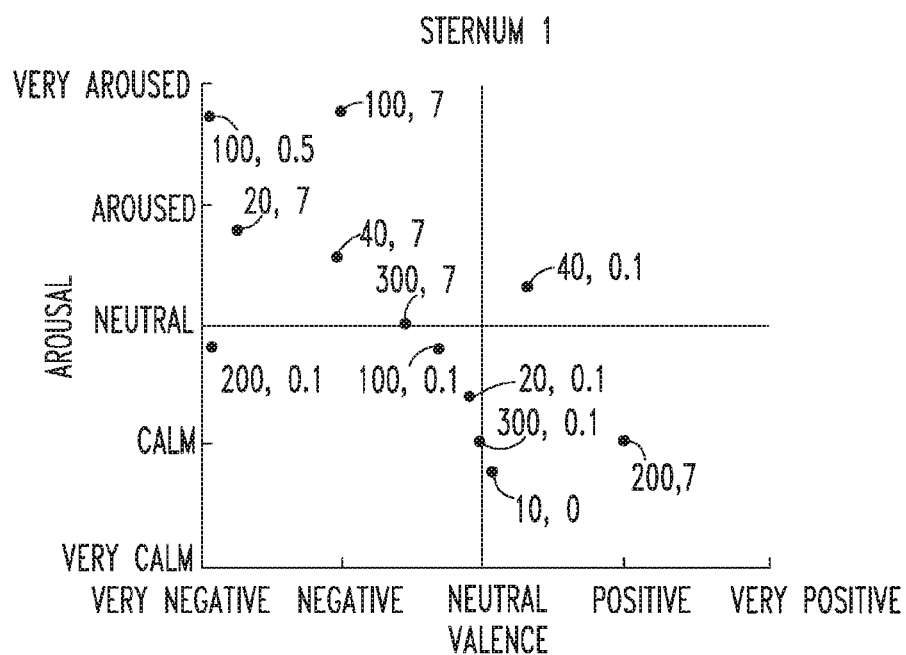
Figure 7D:
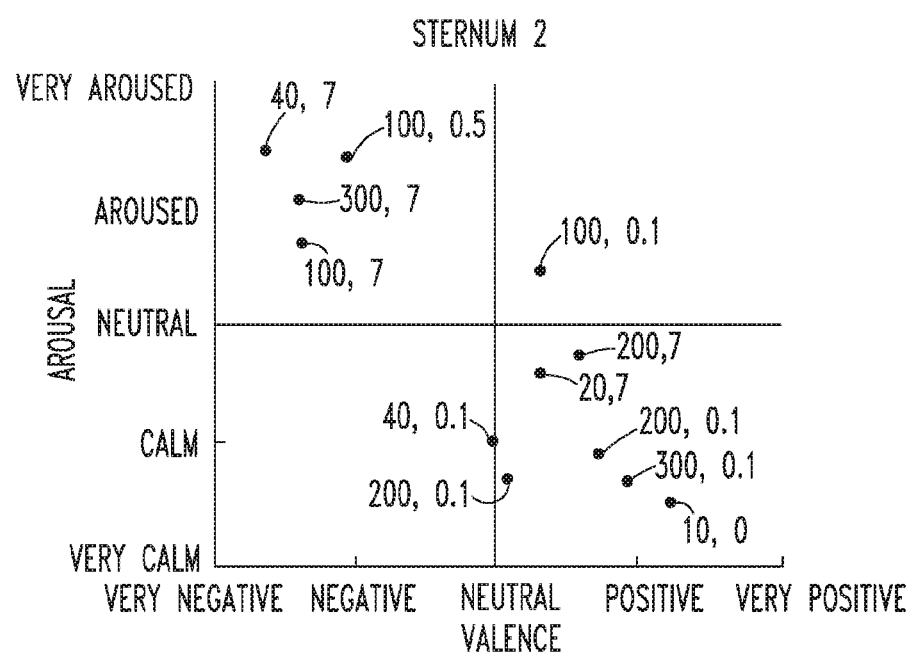

FIG. 6 shows that we can derive a classifier that detects the onset of stress during a stressful serial addition task.

Vocal Detection and Calibration

Figure 5:
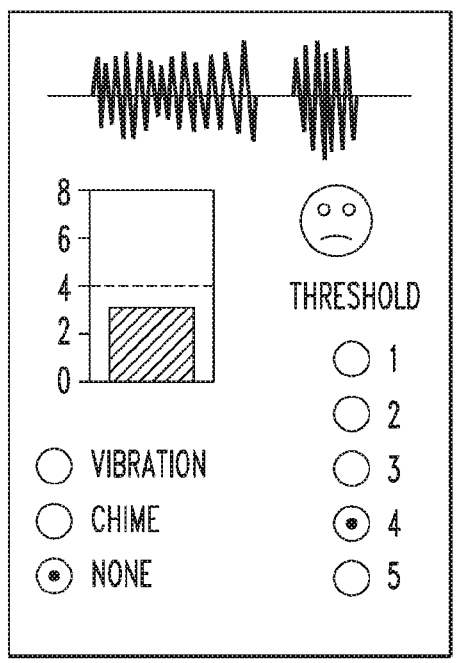
FIG. 5: Example of user interface of software for detection of vocal stress.

FIG. 5 shows an example of implemented software for detection of vocal stress.

One aspect of the vocal stress detection algorithm is that speech is recorded in 5-second segments. These segments are processed to extract common vocal parameters such as speech rate, pitch, mean frequency, frequency of the first fundamental, variance of the first fundamental, etc. using publicly available code. The speech data from any 5-second segment is not saved after parameters are extracted, and thus no lasting voice recordings are made.

Another aspect is that a 4-layer pattern-network classifier was trained to recognize the emotion associated with short vocalizations (neutral, calm, happy, sad, fearful, angry, disgusted, surprised) using the "RAVDESS" speech corpus (http://smartlaboratory.org/ravdess/designfeatures/) preprocessed to be z-scores normalized by the mean of vocalizations and divided by the standard deviation. Outliers were Windsorized to the next good value outside the Tukey Hinges. The network had 15 inputs for vocal parameters, 2 hidden layers with 15 and 10 units respectively, and 8 outputs—one per classified emotion and was trained with a standard back-propagation algorithm. Classification was 30-80% accurate for specific valences depending on the valence.

Another aspect of the algorithm is that extracted speech parameters are normalized by subtracting the mean of a set of six five-second "neutral" calibration vocalizations and dividing by the standard deviation these vocalizations.

Another aspect of the vocal stress detection algorithm is that it begins with a calibration consisting of recording 30 seconds of silence in a specific room. The variance of incoming 5-second vocalizations are, at each iteration, compared to the variance of the "silence" recording. Audio waveforms with variability outside 2 standard deviations (SD) from the silence recording are considered to be vocalizations; otherwise they are considered silence and not categorized.

Another aspect of the vocal stress detection algorithm is that a second calibration records an individual person, who is the subject of measurement, speaking in a neutral tone for 30 seconds.

Another aspect of the algorithm is that when more than a user-selected number of the vocal parameters (the user can select from 2-8 parameters) are outside 2 SD from the mean of neutral vocalizations, and when the person is deemed, via classification based on the RAVDESS corpus classifier, to have a negative tone (fear, sadness, disgust), the software provides user-selected stimulation waveforms to the stimulation generator. This is depicted in the user interface capture from the software that is depicted in FIG. 5 wherein the user has selected a threshold of four parameters, as is indicated by the "THRESHOLD" indicator, and which is reflected by the dashed line in the bar graph of FIG. 5. An exemplary vocal wave pattern is depicted at the top of FIG. 5, and the bar indicator in the bar graph demonstrates that the threshold has not been reached. It is noted that FIG. 5 further depicts the user-selectable option to have either a tactile output in the form of a vibration or an audible output in the form of a chime when the user is determined to be in a stressed state. In the event of such an output, a user can manually enter an input using the buttons to trigger the outputting of the therapeutic stimulation. Alternatively, the user can select "NONE", which is selected in FIG. 5. In the Vibration condition, and in the event of the detected state of the user being stress or another user-specified condition, this will automatically result in the outputting of the therapeutic stimulation.

Stimulation Calibration

The stimulation calibration algorithm performs a customization operation that involves presenting individuals with a plurality of customization stimulations in the form of a range of stimulation parameters and allowing them to rate the emotionality and arousal associated with these types of stimulation. In response to each customization stimulation, the user inputs to the software a number of responses using a single selection on a grid. The number of responses are representative of how the user perceived the customization stimulation on an arousal scale between very calming and very arousing, and are further representative of how the user tolerated the customization stimulation on a valence scale between very negatively and very positively. To best tune stimulation to an individuals' preferences, the software selects stimulation patterns based on these ratings. The pattern which is rated as maximally positive and maximally calming (sqrt of the squared distance on each axis from neutral) is used as the calming stimulation pattern for that individual in the event of detecting that the individual is experiencing a stress condition. The pattern which is maximally arousing, regardless of its valence, is used as the arousing stimulation pattern for that individual in the event of detecting that the individual is experiencing a fatigue condition.

FIGS. 7A, 7B, 7C, AND 7D show that there are reliable overall differences in emotion and arousal as a function of oscillation patterns for the vibrating transducer and that there are individual differences in which patterns are most calming and arousing for different individuals. Each data point in such figures is representative of how the user perceived the customization stimulation on an arousal scale between very calming and very arousing, and additionally how the user tolerated the customization stimulation on a valence scale between very negatively and very positively.

State Storage and Use in "Restoring" Saved States

Physiological parameters in the form of baseline physical parameters associated with named target emotional states (e.g., "stress" or "positive affect calm") can be stored for later recall as targets (triggers stimulation that decreases distance to the state when it is determined that a number of current physical parameters are more than a predetermined distance of those of the target emotional state) or alarms (triggers stimulation that increases distance from the state when it is determined that a number of current physical parameters are within a predetermined distance of those of the target emotional state).

Another aspect of the invention includes software that allows subjective and physiologically based storage of stimulation parameters that optimally yield approach or departure from target or alarm states.

Another aspect of the present invention includes software that allows users to specify potentially new or idiosyncratic target or alarm emotion states for storage in a library which includes associated physiological profiles and stimulation parameters.

Another aspect of the present invention is that physiological profiles can be used to gauge distance from normed and idiosyncratically named categories by the cosine of current physiological parameters with those for calibrated states, e.g., yielding a "Closeness" value C for each parameter, e.g., $C_{GSR}=(GSR_{current}-GSR_{session\_mean})*(GSR_{calibration\ state}-GSR_{calibration\ session\ mean})$ and deriving the "Closeness" to a state as $B_{GSR}*C_{GSR}+B_{HRV}*C_{HRV}+B_{Vocal\ Pitch}*C_{Vocal\ Pitch}$ where associated B weights are derived via neural network classifiers as described herein before.

This algorithm provides distance from target states. Before calibration, a priori rules are used to specify output transduction to optimally restore a state via minimizing distance (e.g., Euclidean) of current data from template vectors as described herein before.

Another aspect of the present invention includes software that allows users to share emotion state names, associated physiological profiles, and stimulation parameters for approaching or avoiding them.

Possible Practical Applications

A source for generating physiologically reactive oscillation patterns (e.g., smartphone) wherein the oscillation patterns are frequencies in the range of 20-300 Hz modulated by frequencies from 0.01-10 Hz.

The source generates oscillations and transmits them via Bluetooth.

Software is used to calibrate and store what vibration patterns maximally yield specific emotional states, including those specified by a user, such as arousal, or positive-affect calm for a given individual, or that individual's state on a given day, to which they would like to return in the future.

This software can store what vibration patterns individuals are using and dynamically update its calibration to "learn" if users choose to use patterns not suggested by the previous calibration.

A Bluetooth receiver for oscillation patterns generated by the source.

A switch, software control, or physiological/vocal measurement device to determine when the oscillation patterns are delivered.

The software computes the magnitude and slope of physiological or vocal measures over a local window (0.5-30 seconds) to determine onsets of emotion state deviations from a neutral state (e.g., stress, fatigue).

The software compares incoming physiological measurements to an individually calibrated profile to determine likelihood of onset of an emotion state and the appropriate reaction.

The software has a calibration routine that requires the individual to attain relaxed/neutral, stressed (e.g., via stressful cognitive task), or fatigued states, and record data for profile derivation.

The software uses machine learning algorithms (e.g., neural networks) to derive individually calibrated emotion state (e.g., stress) indices from the calibration data used as a training set.

The software stores learned physiological patterns in a library that can be recalled in combination with associated stimulation patterns as described to allow "restoration" of "saved" states.

A battery to power the amplifier.

An amplifier that raises the received oscillation patterns to a non-ignorable level.

Transducers that provide one of vibratory and electrical stimulation.

A sleeve for the vibratory transducer that can be removed and washed.

The sleeve may allow the device to be attached to the individual, e.g., via a band or other means for securing the device to the body part without disrupting the transducers functionality.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination. Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of employing a regulatory device to provide stimulation therapy to a user, comprising:
    applying, to an area of a body of a user, a regulatory device;
    detecting, on the regulatory device, an input; and
    responsive to the input, generating with the regulatory device a therapeutic stimulation in the form of vibrational output applied to the area of the body of the user, the therapeutic stimulation comprising a combination of oscillations that include at least a main oscillation at a first frequency in the range of about 20-300 Hz and a modulation oscillation at a second frequency different than the first frequency in the range of about 0.01-10 Hz that together form a beat output.

2. The method of claim 1 wherein:
    the regulatory device further comprises electrodes; and
    the therapeutic stimulation further comprises an electrical output in the form of a pulse-width-modulation waveform.

3. The method of claim 1 wherein the input comprises a physiological parameter of the user.

4. The method of claim 1, further comprising:
    detecting with the regulatory device one or more current physical parameters of the user; and
    analyzing the one or more current physical parameters to determine a physiological state of the user.

5. The method of claim 4, wherein:
    detecting with the regulatory device the one or more current physical parameters of the user comprises detecting a heartbeat signal that is representative of a heartbeat of the user;
    the method further comprises deriving, at least in part from the heartbeat signal, values of the user that are representative of sympathetic or parasympathetic nervous system activity of the user; and
    determining the physiological state of the user comprises using the values derived from the heartbeat signal over a period of time to determine a stress level of the user.

6. The method of claim 4, wherein:
    detecting with the regulatory device the one or more current physical parameters of the user comprises detecting a Galvanic Skin Response (GSR) signal that is representative of a galvanic skin response in the skin of the user; and
    determining the physiological state of the user comprises identifying when a change in the GSR signal is detected over a period of time.

7. The method of claim 6, wherein:
    detecting with the regulatory device the current physical parameters of the user comprises detecting one or more audio parameters that are representative of vocal tone in the user; and
    determining the physiological state of the user comprises identifying when a change in vocal parameters is detected in conjunction with changes in the GSR signal and the values derived from the heartbeat signal.

8. The method of claim 4, wherein:
    detecting with the regulatory device the current physical parameters of the user comprises detecting a vocal signal that is representative of a vocal output of the user;
    the method further comprises deriving, at least in part from the vocal signal, values of the user that are representative of sympathetic or parasympathetic nervous system activity of the user; and
    determining the physiological state of the user is also based at least in part upon the values derived from the vocal signal.

9. The method of claim 1, further comprising, before detecting the input, performing a calibration operation by:
    guiding the user through a plurality of physiological states including at least two of a resting state, a stressed state, and a fatigued state;
    detecting with the regulatory device calibration physical parameters of the user in each state of the plurality of physiological states; and
    deriving an individually calibrated profile for the user based at least in part upon at least some of the calibration physical parameters.

10. The method of claim 9 wherein the deriving of the individually calibrated profile comprises subjecting at least some of the calibration physical parameters to a machine learning algorithm to derive coefficients that are a part of the individually calibrated profile.

11. The method of claim 9, further comprising:
    when detecting the input, detecting with the regulatory device one or more current physical parameters of the user;
    based at least in part upon the one or more current physical parameters and the individually calibrated profile, determining a current physiological state of the user; and when the current physiological state comprises stressed or fatigued, responsive to the determination, triggering the therapeutic stimulation.

12. The method of claim 1, further comprising performing a customization operation by:
   before generating the therapeutic stimulation, outputting with the regulatory device a plurality of customization stimulations, each customization stimulation being in the form of a vibrational output applied to the user's body and comprising a combination of oscillations that include at least a main oscillation at a first frequency in the range of about 20-300 Hz and a modulation oscillation at a second frequency different than the first frequency in the range of about 0.01-10 Hz apart that together form a beat output;
   for each customization stimulation of the plurality of customization stimulations, receiving from the user an input that is representative of how the user perceived the customization stimulation on an arousal scale between very calming and very arousing, and receiving from the user another input that is representative of how the user tolerated the customization stimulation on a valence scale between very negatively and very positively; and
   identifying a particular customization stimulation from among the plurality of customization stimulations as having the greatest combination of being closest to very calming on the arousal scale and very positively on the valence scale; and
   when generating the therapeutic stimulation, generating the particular customization stimulation as the therapeutic stimulation.

13. The method of claim 12, further comprising:
   identifying a specific customization stimulation from among the plurality of customization stimulations as being closest to very arousing on the arousal scale; and
   when generating the therapeutic stimulation, generating the specific customization stimulation as the therapeutic stimulation.

14. The method of claim 1 wherein:
   detecting, on the regulatory device, the input comprises detecting current physical parameters of the user; and
   the method further comprises, based at least in part upon the current physical parameters, determining a state of stress.

15. The method of claim 1 wherein:
   detecting, on the regulatory device, the input comprises detecting current physical parameters of the user; and
   the method further comprises, based at least in part upon the current physical parameters, that user is in a state of fatigue.

16. The method of claim 1, wherein the input comprises current physical parameters of the user and the method further comprises:
   before detecting the input:
   detecting with the regulatory device baseline physical parameters of the user and recording the baseline physical parameters as a target emotional state; and
   making a determination that the current physical parameters exceed a predetermined distance from the target emotional state; and
   based on the determination, triggering the therapeutic stimulation.

17. A regulatory device structured to provide stimulation therapy to a user, the regulatory device comprising:
   a processor;
   a vibratory device; and
   and a storage medium, the storage having stored therein one or more routines which, when executed on the processor, cause the therapeutic apparatus regulatory device to perform operations comprising:
   detecting on the regulatory device an input, and
   responsive to the input, generating with the regulatory device a therapeutic stimulation in the form of vibrational output applied to the user's body, the therapeutic stimulation comprising a combination of oscillations that include at least a main oscillation at a first frequency and a modulation oscillation at a second frequency different than the first frequency that together form a beat output.

18. A non-transitory machine readable storage medium having stored therein instructions which, when executed on a processor of a regulatory device, cause the regulatory device to perform operations comprising:
   detecting on the regulatory device an input; and
   responsive to the predetermined input, generating with the regulatory device a therapeutic stimulation in the form of vibrational output applied to the user's body, the therapeutic stimulation comprising a combination of oscillations that include at least a main oscillation at a first frequency and a modulation oscillation at a second frequency different than the first frequency that together form a beat output.

* * * * *